United States Patent [19]

Paul et al.

[11] Patent Number: 5,141,858
[45] Date of Patent: Aug. 25, 1992

[54] **METHOD FOR THE PRODUCTION OF α(1→2) OLIGODEXTRANS USING *LEUCONOSTOC MESENTEROIDES* B-1299**

[75] Inventors: François B. Paul, Saint Orens, France; Agustin Lopez Mungica Canales, Coyoacan, Mexico; Magali M. Remaud, Romonville-Saint-Agne; Vincent P. Pelenc, Toulouse, France; Pierre F. Monsan, Blagnac, France

[73] Assignee: BioEurope, Toulouse, France

[21] Appl. No.: 548,938

[22] PCT Filed: Dec. 6, 1989

[86] PCT No.: PCT/FR88/00596
§ 371 Date: Jul. 27, 1990
§ 102(e) Date: Jul. 27, 1990

[87] PCT Pub. No.: WO89/07148
PCT Pub. Date: Aug. 10, 1989

[30] Foreign Application Priority Data

Jan. 29, 1988 [FR] France .................. 88/01041

[51] Int. Cl.⁵ .............................. C12P 19/18
[52] U.S. Cl. .......................... 435/97; 435/822
[58] Field of Search ............. 435/74, 97, 822

[56] References Cited

U.S. PATENT DOCUMENTS

2,726,190 12/1955 Koepsell et al. ............... 195/31
4,649,058 3/1987 Schwengers .................. 426/658
4,895,801 1/1990 Kan et al. ..................... 435/101

FOREIGN PATENT DOCUMENTS

749515 5/1956 United Kingdom .

OTHER PUBLICATIONS

R. Eby et al.–Carbolty Dr. Res. 102:131-138 (82).
M. E. Preobrazhenskaya et al.–Chem. Abs. 86:85289 z(77).
I. Shunji et al. Chem. Abs. 88:168503g (78).
Mitsuishi et al. Carb. Res. 127:331-337 (84).
Kobayashi et al. J. Biochem 79:1301-1308 (76).
Preobrazhenskay et al. Chem. Abs. 86:85289z (77).
Jeanes et al., "Characterization and Classification of Dextrans From Ninety-Six Strains of Bacteria," Journal of American Chemical Society, vol. 76, pp. 5041-5052 (1954).
Paul, "Acceptor Reaction of a Highly Purified Dextransucrase with Maltose and Oligosaccharides. Application to the Synthesis of Controlled-Molecular-Weight Dextrans", Carbohydrate Research, vol. 149, pp. 433-441 (1986).
Archives of Biochemistry and Biophysics 104, (1964) 305-313, Hiroshi Suzuki et al.
Agric. Biol. Chem., 49 (2) (1985) 501-507, Ikuko Yokoyama et al.
Carbohyd. Res. 25 (1972) 443-451, Keiko Sakakibara et al.
Carbohyd. Res., 31 (1973) 277-287, Hideki Miyaji et al.

*Primary Examiner*—Douglas W. Robinson
*Assistant Examiner*—S. Saucier
*Attorney, Agent, or Firm*—Breiner & Breiner

[57] ABSTRACT

A method for the production of oligodextrans containing an α(1→2) bond which uses glycosyltransferase from *Leuconostoc mesenteroides*, particularly strain B-1299, sucrose and an accepter moiety such as glucose, maltose, isomaltose, isomaltotriose or methyl α-glucose. Optionally, this product may be further treated with an endodextranase or glucosamylase.

9 Claims, No Drawings

METHOD FOR THE PRODUCTION OF α(1→2) OLIGODEXTRANS USING *LEUCONOSTOC MESENTEROIDES* B-1299

The invention relates to a process for the enzymatic preparation of oligodextrans used in the production of sugar substitutes and to novel oligodextrans.

It is known to prepare dextrans of high molar mass, greater than one million (degree of polymerization greater than 6000 units of glucose) by the action of the lactic bacterium Leuconostoc mesenteroides on sucrose. It is also known that certain strains of this bacterium produce dextrans containing glucoside α(1→2) bonds, which constitute the branching points in these dextrans.

It was not known, however, prior to the present invention to carry out the enzymatic synthesis of oligodextrans (dextrans with a low degree of polymerization) containing at least one glucoside α(1→2) bond directly using sucrose and a sugar acceptor of glucose residues originating from sucrose.

The object of the present invention is to provide just such a process.

More precisely, the invention relates to a process for the preparation of a mixture of oligodextrans containing at least one α(1→2) glucoside bond and containing a major proportion of oligodextrans of the general formula (O-α-D-glucopyranosyl-(1→2))$_m$(O-α-D-glucopyranosyl-(1→6))$_n$A where A is the residue of a sugar acceptor of glucose chosen from amongst maltose, isomaltose, isomaltotriose, methyl α-glucoside and glucose, m is from 1 to 10 and n is from 1 to 30, the position of the α(1→2) glucoside bond or bonds being arbitrary, characterized in that sucrose and a sugar acceptor of glucose chosen from the group comprising maltose, isomaltose, isomaltotriose, methyl α-glucoside and glucose are brought into contact in the presence of glucosyltransferase enzyme extracted from at least one strain of the lactic bacterium Leuconostoc mesenteroides capable of producing, by fermentation, a dextran containing α(1→2) glucoside bonds, for approximately 2 to 48 hours in an aqueous medium.

The position of the glucoside α(1→2) bond or bonds in the formula indicated above is variable as a function, in particular, of the nature of group A and of the molar mass of the oligodextran, which itself is dependent on the reaction conditions. These bonds may, for example, be on the main chain, on the branches or may constitute the branching points in the oligodextran.

Non-restrictive examples of suitable strains of the lactic bacterium Leuconostoc mesenteroides are the following: NRRL B-1299, B-1399, B-1397, B-1298, B-1396, B-1424, B-1382, B-1149 and B-523.

Some of the oligodextrans (sometimes also called oligosaccharides) produced by the process of the invention are novel compounds. The preparation of O-α-D-glucopyranosyl-(1→2)-O-α-D-glucopyranosyl-α(1→6)-D-glucose trisaccharide by acetolysis of dextran NRRL B-1397 has, however, been described by K. Sakakibara et al. in Carbohydrate Research, 25 (1972), pages 443-451. Likewise, Y. Mitsuishi et al., in Carbohydrate Research, 127 (1984), pages 331-337, have described oligosaccharides branched by means of an α(1→2) glucoside bond.

The invention thus also relates to oligodextrans of the general formula (O-α-D-glucopyranosyl-(1→2))$_m$(O-α-D-glucopyranosyl-(1→6))$_n$A where A is the residue of a sugar acceptor of glucose chosen from amongst maltose and methyl α-glucoside, m is from 1 to 3 and n is from 1 to 10, the position of the α(1→2) glucoside bonds being arbitrary, as novel products.

The oligodextrans produced by the process of the invention which contain an α(1→2) glucoside bond which is located at their non-reducing end or which constitutes a branching point in the oligodextran, whether novel in themselves or not, are particularly resistant to enzymatic hydrolysis by glucohydrolase enzymes, such as endodextranase and glucoamylase, this resistance being due to the presence of this rare α(1→2) glucoside bond located at their non-reducing end or constituting a branching point in the oligodextran.

This property makes them useful as fillers or extenders in sugar substitutes which are metabolizable by man only slightly or not at all. They may therefore be used in low-calorie foodstuff formulations, mixed with a strong sweetener, such as aspartame or equivalent.

The oligosaccharides of the invention may also promote the growth and the development of certain beneficial microorganisms of the intestinal flora. This property may make them equally useful as additives in animal feeds (additives of zootechnic value) and for human foodstuffs (dietetics and nutrition).

The invention thus also relates to the use of a mixture of oligodextrans containing at least one α(1→2) glucoside bond located at their non-reducing end or constituting a branching point in the oligodextran, which contain a major proportion of oligodextrans of the general formula O-α-D-glucopyranosyl-(1→2)$_m$(O-α-D-glucopyranosyl- (1→6))$_n$A where A is the residue of a sugar acceptor of glucose chosen from amongst maltose, isomaltose, isomaltotriose, methyl α-glucoside and glucose, m is from 1 to 10 and n is from 1 to 30, the position of the α(1→2) glucoside bond or bonds being arbitrary, as fillers in sugar substitutes or as foodstuff additives.

As indicated above, the enzymatic synthesis reaction is carried out in the presence of glucosyltransferase enzyme (E.C:2.4.1.5) extracted from strains of the bacterium Leuconostoc mesenteroides capable of producing, by fermentation, a dextran containing α(1→2) glucoside bonds. This reaction may be represented by the global equation:

glucosyltransferase sucrose + sugar acceptor → oligodextrans + fructose

Suitable strains are, inter alia, the NRRL B-1299, B-1399, B-1397, B-1298, B-1396, B-1424, B-1382, B-1149 and B-523 strains. These strains are obtainable from the N.R.R.C. (Northern Regional Research Center), the address of which is as follows: Agricultural Research Service, U.S. Department of Agriculture, 1815 North University Street, Peoria, Ill. 61604, USA. They were characterized at the start of the 1950's using a selection of microorganisms isolated from soil. They have been indexed, amongst others, in the following publication:

"Characterization and classification of dextrans from ninety-six strains of bacteria", A. Jeanes et al. (1954), J. Amer. Chem. Soc. 76, 5041-5052.

It goes without saying that it would also be possible to use, in place of the strains cited above, strains derived from these and obtained by mutagenesis in a conventional manne, i.e. by irradiation of the strains or by the action of a chemical agent on the said strains, followed by culture of the surviving individuals, or obtained by selection of natural mutants. For the purpose of the invention, these mutant strains are considered as equivalent to the strains cited above.

Glucosyltransferase can be obtained by culturing an appropriate strain of the lactic bacterium Leuconostoc mesenteroides, such as the NRRL B-1299 strain, on a suitable nutrient medium containing, in particular, sucrose in order to induce the production of the glucosyltransferase. After growth of the bacterium, the enzymatic activity is extracted by the addition of polyethylene glycol so as to precipitate and concentrate the various forms of glucosyltransferase: extracellular, bound to cells and to insoluble polysaccharides, and intracellular. This enzymatic preparation then contains whole cells of L. mesenteroides B-1299. Known techniques of cell breaking may be used at the end of the culture to augment the enzymatic activity on the one hand, and to destroy the cells on the other hand (mechanical crushing, use of chemical agents or enzymatic agents (lysozyme, . . . )). However, this operation is not strictly necessary. The extraction of the enzymatic activity by polyethylene glycol is carried out a second time after having redissolved the first precipitate (obtained after the first extraction), for example with the aid of a 20 mM sodium acetate buffer of pH 5.4, containing 0.02 g/l calcium chloride. The second precipitate contains all the enzymatic activity. It can be lyophilized or frozen in concentrated form without loss of activity. Other purification techniques may be used, such as centrifugation, ultrafiltration or a chromatographic process.

The enzymatic synthesis of oligodextrans is carried out with the aid of this enzymatic preparation or of a fraction of this preparation corresponding to a specific form of the enzyme (intracellular enzyme, after breaking of the cells, extracellular enzyme bound to insoluble polymers, soluble extracellular enzyme) in the presence of sucrose, which constitutes the substrate of the reaction, and of a sugar acting—as a glucose acceptor, such as maltose (or a material rich in maltose, such as a starch hyrolysis product), isomaltose, methyl α-glucoside, isomaltotriose or glucose (or a material rich in glucose, such as a starch hydrolysis product).

By way of example, the reaction can be carried out at between 5° and 45° C., preferably between about 20° and 30° C. The pH of the reaction is between 4.5 and 7, preferably between 5 and 6. The reaction time is usually between about 2 and 48 hours; it depends on the concentration of the enzyme in the synthesis medium. Preferably, the enzyme concentration is 0.20 to 1 U/ml, but it could be higher if desired. One enzymatic unit (U) is defined as the quantity of enzyme necessary to produce 1 micromole of fructose per minute under the following standard conditions for the measurement of the activity:
sucrose: 100 g/l
20 mM sodium acetate buffer, pH 5.2
30° C.

The proportions of sucrose and of sugar glucose acceptor are not very critical. By way of example, a sucrose concentration of from 20 to 600 g/l and a sugar glucose acceptor concentration of from 10 to 300 g/l may be used. The highest yields are obtained from the oligodextrans synthesis when the ratio of the sucrose concentration, expressed in g/l, to the acceptor concentration, expressed in g/l, is between 0.5 and 10 and preferably between 2 and 4.

The enzyme may be used either in the free form (discontinuous process) or incorporated inside a cross-linked gel (calcium alginate gel, for example) or bound in a covalent manner to an insoluble support. If the enzyme is immobilized, it may then be used in an appropriate reactor (fixed bed reactor, fluidized bed reactor, etc. . . . ) for the continuous production of oligodextrans.

After the action of the enzyme, the reaction medium may be analysed by a high performance liquid chromatography (HPLC) method with inverse phase separation of the oligodextrans (for example the micro-Bondapack C18 column from Millipore-Waters), elution being effected with ultrapure water or with a water/methanol mixture (% methanol between 0 and 6% (v/v)). This quantitative method enables all of the oligodextrans with a degree of polymerization of between about 2 and 20 to be separated.

The assay of the reducing sugars produced in the course of the reaction may be effected with D.N.S. reagent (sodium dinitrosalicylate in an alkaline medium).

The reaction mixture obtained comprises oligodextrans containing at least one $\alpha(1\rightarrow2)$ glucoside bond, oligodextrans which do not contain such a bond, fructose and unaltered sugar glucose acceptor.

The oligodextrans containing an $\alpha(1\rightarrow2)$ glucoside bond may make up about 30 to 55% of the total oligodextrans.

The synthesis and purification process may be adapted in accordance with the molar mass of the oligodextrans sought. In particular, the mean molar mass of the synthesis medium, being higher the higher this ratio. After oligodextrans depends on the sucrose/acceptor ratio in the synthesis medium, being higher the higher this ratio. After synthesis, the fructose may be kept in the reaction medium or separated by a chromatographic ion exchange technique.

Likewise, it should be mentioned that certain additives may be added to the synthesis medium in order to increase the proportion of oligodextrans containing an $\alpha(1\rightarrow2)$ bond, such as certain water-miscible solvents, such as polyethers, like monoglyme, diglyme, etc., and also certain salts such as magnesium chloride, calcium chloride, etc. . . .

Advantageously, if it is desired to eliminate the oligodextrans which do not contain an $\alpha(1\rightarrow2)$ glucoside bond from the reaction medium, the latter may be subjected to the action of hydrolases such as the glucoamylase of Aspergillus niger and/or the endodextranase of Penicillium sp. in order to effect the total hydrolysis of the oligodextrans which do not contain an $\alpha(1\rightarrow2)$ bond. In contrast, the oligodextrans containing an $\alpha(1\rightarrow2)$ bond, in particular those with a degree of polymerization of 4, 5, 6 and 7 (abbreviated D.P. 4, D.P.5, D.P.6 and D.P.7), resist hydrolysis. After the action of the hydrolases, the reaction medium contains glucose, fructose and the oligodextrans containing one or more $\alpha(1\rightarrow2)$ bonds. The glucose and the fructose may be separated, if desired, from the oligodextrans by chromatography, for example with the aid of a cationic exchange resin in the calcium form. The fractions containing the oligodextrans are concentrated under reduced pressure, demineralized, filtered on active charcoal and then dried by lyophilization or by atomization. The final product is a white powder which is highly soluble in water (solubility: 70%, m/m) without a sugar taste, of neutral pH, and contains 95% by weight or more of oligodextrans containing one or more α(1→2) glucoside bonds.

The non-limiting examples which follow are given with a view to further illustrating the present invention.

EXAMPLE 1

(a) Production and Purification of Glucosyltransferase from L. Mesenteroides B-1299

The L. mesenteroides B-1299 strain is stored in lyophilized form or frozen in the presence of 10% (v/v) glycerol.

It is cultured in the following culture medium (standard medium):

sucrose: 40 g/l
yeast extract: 20 g/l
dipotassium phosphate: 20 g/l (added in the form of a solution of which the pH has been adjusted to 6.9 with the aid of pure orthophosphoric acid)
magnesium sulfate. $7H_2O$: 0.2 g/l
manganese sulfate. $H_2O$: 0.01 g/l
calcium chloride. $2H_2O$: 0.02 g/l
sodium chloride: 0.01 g/l
iron sulfate. $7H_2O$: 0.01 g/l The pH of the culture medium is 6.9. The culture medium and the monopotassium phosphate solution have been previously sterilized by heat (121° C., 20 minutes). If the pH is not adjusted during the culture, the medium acidifies as the growth of the bacterium proceeds. At the end of the culture, the pH may reach 4.5. It is preferable to adjust the pH to a higher value of between 5 and 6.5. Adjustment of the pH is carried out with the aid of 2N sodium hydroxide or of an alkaline solution of sucrose (400 g/l sucrose; 2N sodium hydroxide). This latter solution is advantageous because it enables the cellular density of the culture and the production of the enzyme to be increased slowly.

Additives such as maltose (20 g/l) and the surface-active agent Tween ® (1%) promote the excretion of the enzyme in the extracelluar medium in a soluble form.

Table 1 over summarizes the results of three culture tests carried out under various conditions.

The temperature of the culture medium is 27° C. Stirring is at 500 rpm and aeration is at 1 vvm.

After culturing for 6 h 30, the enzyme concentration in the culture medium of test 3 is 4 U/ml, of which 0.6 U/ml is in the soluble and extracellular enzymatic form. 85% of the glucosyltransferase is associated with cells and/or with polysacchardies in the form of insoluble aggregates.

After growth, the various forms of the enzyme are extracted from the culture medium by precipitation in the presence of low molecular weight polyethylene glycol (PEG 1500). All of the enzyme activity precipitates simultaneously with the polysaccharide produced by the bacterium and the cells, while the PEG 1500 concentration reaches 20% (m/v).

The precipitated fraction is centrifuged (10 minutes, 10,000 g) or recovered after sedimentation (12 hours, 4° C., in the presence of a bacteriostatic agent such as sodium sulfite in a concentration of 1 g/liter or sodium benzoate in a concentration of 2 g/liter). After two successive extractions with polyethylene glycol the enzymatic preparation is lyophilized. The yield from extraction of the enzyme is close to 100%.

(b) Enzymatic Synthesis of Oligodextrans with Soluble and Insoluble Glucosyltransferase from L. mesenteroides B-1299

The synthesis is carried out under the following conditions:

sucrose: 100 g/l
maltose: 50 g/l
temperature: 30° C.
20 mM sodium acetate buffer, pH 5.2
sodium nitride: 0.5°/oo (bactericide)
enzyme concentration: 0.3 U/ml After 20 hours reaction, the enzyme is inactivated by heat (30 minutes, 80° C.) and the oligodextrans are then analysed by the HPLC method described above. The results are summarized in Table 2.

TABLE 2

Composition of reaction medium after action of soluble and insoluble glucosyltransferase from L. mesenteroides B-1299

| Sugars | Concentration, g/l |
| --- | --- |
| Fructose | 52.0 |
| Maltose | 15.3 |
| Panose (trisaccharide) | 16.6 |
| Oligodextran of D.P. 4 | 14.9 |
| Oligodextran of D.P. 4 containing an α(1 → 2) bond | 5.3 |
| Oligodextran of D.P. 5 | 7.0 |
| Oligodextran of D.P. 5 containing an α(1 → 2) bond | 18.0 |

TABLE 1

| CULTURE CONDITIONS | Total enzymatic activity, U/ml | Soluble extracellular activity, U/ml | Concentration of insoluble matter (cells + polysaccharides) mg/ml | Insoluble activity, U/mg |
| --- | --- | --- | --- | --- |
| Test 1: conical flask no adjustment of the pH of the standard medium | 3.5 | 0.35 | 7.9 | 0.4 |
| Test 2: 2 liter fermenter standard medium + maltose (20 g/l) + Tween ® (1%) no pH adjustment | 2.75 | 0.6 | 4.3 | 0.5 |
| Test 3: 2 liter fermenter standard medium + maltose (20 g/l) + Tween ® (1%) + pH adjustment to 5.6 by the addition of alkaline sucrose (400 g/l sucrose: 2N sodium hydroxide) | 4.0 | 0.6 | 8.4 | 0.4 |

TABLE 2-continued

Composition of reaction medium after action of soluble and insoluble glucosyltransferase from L. mesenteroides B-1299

| Sugars | Concentration, g/l |
|---|---|
| Oligodextran of D.P. >5 containing at least one α(1 → 2) bond | 5.9 |
| Yield of oligodextrans containing an α(1 → 2) bond* | 30% |
| Yield of the acceptor reaction** | 84% |

The yields are expressed in the following way:

$$(*) \quad \frac{(\text{oligodextrans } \alpha(1 \to 2)), \text{ g/l}}{0.474 \times (\text{sucrose}) + (\text{maltose}), \text{ g/l}}$$

$$(**) \quad \frac{(\text{total oligodextrans}), \text{ g/l}}{0.474 \times (\text{sucrose}) + (\text{initial acceptor} - \text{residual acceptor}), \text{ g/l}}$$

(c) Enzymatic Synthesis of Oligodextrans with Soluble and Insoluble Glucosyltransferase from L. Mesenteroides B-1299 in the Presence of Additives Three syntheses 1, 2 and 3 were carried out under the following common conditions:
sucrose: 100 g/l
maltose: 33 g/l
20 mM sodium acetate buffer, pH 5.2
sodium nitride: 0.5°/oo
enzyme concentration: 1 U/ml
temperature: 30° C. but with the following differences:
 synthesis 1: incubation period: 6 hours (without additive)
 synthesis 2: incubation period: 23 hours, in the presence of 500 mM magnesium chloride and 5 mM calcium chloride.
 synthesis 3: incubation period: 23 hours, in the presence of 300 mM calcium chloride.

After the incubation period indicated, the enzyme is inactivated by heat (30 minutes, 80° C.) and the oligodextrans are then analyzed by the HPLC method described above. The results are summarized in Table 3.

The rate of the enzymatic reaction is severely slowed in the presence of high concentrations of salts (calcium chloride and magnesium chloride). Nevertheless, a substantial increase in the population of oligodextrans containing at least one α(1→2) bond is observed relative to the sample synthesis (carried out without additive).

TABLE 3

Composition of the reaction medium after the action of soluble and insoluble glucosyltransferase from L. mesenteroides B-1299 in the presence of additives

| | Synthesis 1 | Synthesis 2 | Synthesis 3 |
|---|---|---|---|
| Fructose | 53.7 | 47.3 | 54.6 |
| Maltose, leucrose | 7.9 | 11.0 | 8.9 |
| Panose | 6.6 | 9.7 | 6.0 |
| Oligodextran of D.P. 4 | 8.3 | 7.7 | 6.0 |
| Oligodextran of D.P. 4 containing an α(1 → 2) bond | 1.9 | 5.9 | 3.7 |
| Oligodextran of D.P. 5 | 5.0 | 5.4 | 4.0 |
| Oligodextran of D.P. 5 containing an α(1 → 2) bond | 12.2 | 22.8 | 17.9 |
| Oligodextran of D.P. > 5 containing an α(1 → 2) bond | 3.8 | 8.8 | 11.2 |
| Yield of oligodextrans containing an α(1 → 2) bond | 22% | 47% | 41% |
| Yield of the acceptor reaction | 52% | 75% | 61% |

EXAMPLE 2

Synthesis of Oligodextrans with the Soluble Glucosyltransferase from L. Mesenteroides B-1299

After centrifuging the culture medium in order to remove the insoluble cells and polymers (10,000 g, 20 minutes), the supernatant is subjected to a liquid-liquid extraction with polyethylene glycol 1,500 in accordance with the method described in Example 1. The yield from the extraction of the glucosyltransferase is greater than 85%. This operation was carried out twice. The enzyme is then frozen or lyophilized in 20 mM sodium acetate buffer, pH 5.2.

The synthesis is carried out under the following conditions:
sucrose: 100 g/l
maltose: 50 g/l
temperature: 30° C.
20 mM sodium acetate buffer, pH 5.2
enzyme concentration: 0.5 U/ml
reaction time: 4 hours.

After the sucrose has been totally consumed by the glucosyltransferase, the enzyme is denatured by heat (30 minutes, 80° C.). The analysis of the oligodextrans present in the reaction medium is carried out by the HPLC method described above. The results are expressed in Table 4.

TABLE 4

Composition of the reaction medium after action of the soluble glucosyltransferase from L. mesenteroides B-1299

| Sugars | Concentration g/l |
|---|---|
| Fructose | 50.5 |
| Maltose | 11.6 |
| Panose | 17.4 |
| Oligodextran of D.P. 4 | 19.0 |
| Oligodextran of D.P. 4 containing an α(1 → 2) bond | 3.1 |
| Oligodextran of D.P. 5 | 9.9 |
| Oligodextran of D.P. 5 containing an α(1 → 2) bond | 18.2 |
| Oligodextrans of D.P. > 5 containing at least one α(1 → 2) glucoside bond | 13.6 |
| Yield of oligodextrans containing at least one α(1 → 2) bond | 36% |
| Yield of the acceptor reaction | 95% |

The yields do not take account of the oligodextrans of D.P. greater than or equal to 7, which do not appear on the chromatograms obtained by this method.

EXAMPLE 3

Synthesis of oligodextrans with the insoluble glucosyltransferase from L. mesenteroides B-1299

The culture medium is centrifuged (20 minutes, 10,000 m, 4° C.) and the residue after centrifuging is washed several times with the aid of 20 mM sodium acetate buffer of pH 5.2. The solution is then lyophilized in order to eliminate all microbial proliferation.

The synthesis of the oligodextrans is carried out under the following conditions:

sucrose: 100 g/l
maltose: 50 g/l
temperature: 30° C.
20 mM sodium acetate buffer, pH 5.2
sodium nitride: 0.5°/oo
enzyme concentration: 0.9 U/ml After incubating for 8 hours, the sucrose is totally consumed. Table 5 summarizes the composition of the oligodextrans in the synthesis medium.

TABLE 5

Composition of the reaction medium after action of the insoluble glucosyltransferase (associated with cells) from L. mesenteroides B-1299

| Sugars | Concentration, g/l |
| --- | --- |
| Fructose | 51.2 |
| Maltose | 22.0 |
| Panose | 12.8 |
| Oligodextrans of D.P. 4 | 9.6 |
| Oligodextrans of D.P. 4 containing an α(1 → 2) bond | 5.7 |
| Oligodextrans of D.P. 5 | 3.7 |
| Oligodextrans of D.P. 5 containing an α(1 → 2) bond | 13.9 |
| Oligodextrans of D.P. > 5 containing at least one α(1 → 2) bond | 3.7 |
| Yield of oligodextrans containing at least one α(1 → 2) bond | 24% |
| Yield of the acceptor reaction | 65% |

EXAMPLE 4

Influence of the concentration of the soluble glucosyltransferase from L. mesenteroides B-1299 on the synthesis of oligodextrans Experimental conditions:
sucrose: 100 g/l
maltose: 50 g/l
20 mM sodium acetate buffer, pH 5.2
temperature: 30° C.

Three concentrations of enzyme were used: 0.17, 0.5 and 2 U/ml. After total consumption of the sucrose, the 3 reaction media were analyzed. The results are identical for the three syntheses, both in respect of the yield of the acceptor reaction and in respect of the yield of oligodextrans containing at least one α(1→2) bond.

EXAMPLE 5

Influence of pH on the enzymatic syntnesis of oligodextrans

Experimental conditions:
sucrose: 100 g/l
maltose: 50 g/l
temperature: 30° C.
enzyme concentration: 1 U/ml
30 mM sodium phosphate citrate buffer Three pH's were tested: 5.2, 6.0 and 6.4. The activity of the soluble and insoluble enzyme falls slightly when the pH is greater than 6.0. However, no significant difference due to the pH value is observed with regard to to the oligodextran composition of the reaction medium.

EXAMPLE 6

Synthesis of oligodextrans in the presence of a mixture of isomaltose and isomaltotriose as acceptor with insoluble glucosyltransferase from L. mesenteroides B-1299

Experimental conditions:
sucrose: 100 g/l
acceptor: 50 g/l composition of the acceptor: isomaltose: 59% isomaltotriose: 36% glucose: 5%
temperature: 30° C.
sodium nitride: 0.5°/oo
20 mM sodium acetate buffer, pH 5.2
enzyme concentration: 1 U/ml After consumption of the sucrose, the analysis of the reaction medium is carried out with the aid of the HPLC method described above (Table 6).

TABLE 6

Composition of the reaction medium after action of the insoluble glucosyltransferase from L. mesenteroides B-1299

| Sugars | Concentration, g/l |
| --- | --- |
| Fructose | 53.0 |
| Isomaltose | 15.0 |
| Isomaltotriose | 6.1 |
| Oligodextrans of D.P. 4 containing an α(1 → 2) bond | 10.4 |
| Isomaltotetraose | 2.4 |
| Oligodextrans of D.P. 5 containing an α(1 → 2) bond | 9.4 |
| Yield of oligodextrans containing at least one α(1 → 2) bond | 20.5% |
| Yield of the acceptor reaction | 29.0% |

EXAMPLE 7

Synthesis of oligodextrans in the presence of methyl α-glucoside with the glucosyltransferase from L. mesenteroides B-1299

Experimental conditions:
sucrose: 100 g/l
methyl α-glucoside: 50 g/l
other conditions: see Example 6.

After consumption of the sucrose, HPLC analysis of the reaction medium gives the following results (Table 7).

TABLE 7

Composition of the reaction medium after action of the insoluble glucosyltransferase from L. mesenteroides B-1299

| Sugars | Concentration, g/l |
| --- | --- |
| Fructose | 53.0 |
| Methyl α-glucoside | 34.0 |
| Methyl isomaltoside | 4.8 |
| Methyl oligodextrans containing an α(1 → 2) bond | 9.3 |
| Methyl isomaltotrioside | 1.4 |
| Methyl isomaltotetraoside | 0.8 |
| Yield of oligodextrans containing at least one α(1 → 2) bond | 10% |
| Yield of the acceptor reaction | 26% |

EXAMPLE 8

Enzymatic synthesis of oligodextrans in the presence of variable concentrations of sucrose with the soluble and insoluble glucosyltransferase from L. mesenteroides B-1299

Experimental conditions:
temperature: 30° C.
20 mM sodium acetate buffer, pH 5.2
sodium nitride: 0.5°/oo
sucrose/maltose ratio: 3
Synthesis 1:
dry material: 20% (w/w)
sucrose: 15% (w/w)
maltose: 5% (w/w)
enzyme concentration: 0.6 U/ml
Synthesis 2:

dry material: 35% (w/w)
sucrose: 26% (w/w)
maltose: 9% (w/w)
enzyme concentration: 1.2 U/ml
  Synthesis 3:
dry material: 40% (w/w)
sucrose: 30% (w/w)
maltose: 10% (w/w)
enzyme concentration: 1.8 U/ml After 21 hours reaction, the enzyme is inactivated by heat (30 minutes, 80° C.). The HPLC analysis of the reaction medium is given in Table 8.

TABLE 8

Composition of the 3 synthesis media after action of soluble and insoluble (associated with cells) glucosyltransferase from L. mesenteroides B-1299

| | Concentration, g/l | | |
|---|---|---|---|
| | Synthesis 1 | Synthesis 2 | Synthesis 3 |
| Fructose | 90.0 | 150.0 | 180.0 |
| Maltose | 8.7 | 9.7 | 11.9 |
| Leucrose | 6.3 | 13.9 | 20.4 |
| Panose | 11.7 | 17.5 | 22.9 |
| Oligodextran D.P. 4 | 14.8 | 25.5 | 35.2 |
| Oligodextran D.P. 4 containing 1 $\alpha(1 \to 2)$ bond | 5.7 | 10.1 | 13.5 |
| Oligodextran D.P. 5 | 10.6 | 17.9 | 20.1 |
| Oligodextran D.P. 5 containing 1 $\alpha(1 \to 2)$ bond | 28.9 | 44.1 | 53.4 |
| Oligodextrans D.P. $\geq$ 5 containing at least 1 $\alpha(1 \to 2)$ bond | 15.1 | 36.6 | 46.2 |
| Yield of oligodextrans containing one $\alpha(1 \to 2)$ bond | 39% | 40.5% | 38% |
| Yield of the acceptor reaction | 76% | 75% | 70% |

The synthesis medium is then subjected to the action of a mixture of glucoamylase from A. niger (2 U/ml) and endodextranase from Penicillium sp. (17 U/ml) for 6 hours at 40° C. The enzymatic reaction is stopped by heating at 90° C. for 30 minutes. Glucose and fructose are removed by chromatography on an exchange resin in the calcium form.

The concentration of oligodextrans containing an $\alpha(1 \to 2)$ glucoside bond in the reaction medium is 57 g/l for synthesis 1, 107 g/l for synthesis 2 and 122 g/l for synthesis 3.

The distribution of the oligodextrans is as follows:

| | Synthesis 1 % | Synthesis 2 % | Synthesis 3 % |
|---|---|---|---|
| Oligodextrans of D.P. 4 containing an $\alpha(1 \to 2)$ bond | 24 | 26 | 30 |
| Oligodextrans of D.P. 5 containing an $\alpha(1 \to 2)$ bond | 69 | 65 | 57 |
| Oligodextrans of D.P. 6 containing an $\alpha(1 \to 2)$ bond | 4 | 5 | 7 |
| Oligodextrans of D.P. 7 containing an $\alpha(1 \to 2)$ bond | 3 | 4 | 6 |

EXAMPLE 9

Synthesis of oligodextrans in the presence of a glucose sirup rich in maltose (Nutriose R 725) by the soluble and insoluble glucosyltransferase from L. mesenteroides B-1299

Nutriose R 725 is a product of Roquette Frères (Lestrem, France), which has a high content of maltose and maltotriose.

Means composition of the glucose sirup Nutriose R 725:
dry material: 68% (w/w)
glucose: 1.5%
maltose: 77%
maltotriose: 20%
products with a D.P. $\geq$ 4: 1.5%

This glucose sirup was used as acceptor under the following conditions:
  Synthesis 1:
sucrose concentration: 100 g/l
Nutriose R 725: 68 g/l
sucrose/maltose ratio: 2
enzyme concentration: 0.3 U/ml
other conditions: see Example 8
  Synthesis 2:
sucrose concentration: 100 g/l
Nutriose R 725: 42 g/l
sucrose/maltose ratio: 3
enzyme concentration: 0.3 U/ml
other conditions: see Example 8

After incubating for 21 hours, the reaction medium is analyzed by HPLC. The results are summarized in Table 9.

TABLE 9

Composition of the reaction medium after action of the soluble and insoluble glucosyltransferase from L. mesenteroides B-1299

| | Concentration, g/l | |
|---|---|---|
| | Synthesis 1 | Synthesis 2 |
| Fructose | 53.0 | 52.0 |
| Maltose | 18.2 | 9.7 |
| Maltotriose | 7.4 | 4.8 |
| Panose | 21.7 | 8.7 |
| Oligodextran of D.P. 4 | 14.3 | 8.2 |
| Oligodextran of D.P. 4 containing an $\alpha(1 \to 2)$ bond | 4.3 | 2.0 |
| Oligodextran of D.P. 5 | 4.9 | 4.6 |
| Oligodextran of D.P. 5 containing an $\alpha(1 \to 2)$ bond | 15.0 | 12.9 |
| Oligodextrans of D.P. > 5 (containing at least one $\alpha(1 \to 2)$ bond | 3.8 | 8.5 |
| Yield of oligodextrans containing an $\alpha(1 \to 2)$ bond | 21% | 26% |
| Yield of the acceptor reaction | 74% | 60% |

The synthesis medium is then subjected to the action of a mixture of glucoamylase from A. niger (2 U/ml) and endodextranase from Penicillium sp. (17 U/ml) for 6 hours at 40° C. The enzymatic reaction is stopped by heating at 90° C. for 30 minutes. Glucose and fructose are removed by chromatography on an exchange resin in the calcium form.

The concentration of oligodextrans containing an $\alpha(1 \to 2)$ glucoside bond in the reaction medium is 30 g/l for synthesis 1 and 35 g/l for synthesis 2.

| The distribution of the oligodextrans is as follows: | | |
|---|---|---|
| | Synthesis 1 % | Synthesis 2 % |
| Oligodextrans of D.P. 4 containing an $\alpha(1 \to 2)$ bond | 23 | 23 |
| Oligodextrans of D.P. 5 containing an $\alpha(1 \to 2)$ bond | 72 | 70 |

-continued

The distribution of the oligodextrans is as follows:

|  | Synthesis 1 % | Synthesis 2 % |
|---|---|---|
| Oligodextrans of D.P. 6 containing an α(1 → 2) bond | 3 | 4 |
| Oligodextrans of D.P. 7 containing an α(1 → 2) bond | 2 | 3 |

EXAMPLE 10

Hydrolysis of oligodextrans by the glucoamylase from A. niger or a mixture of the glucoamylase from A. niger and the endodextranase from Penicillium sp.

The various reaction media from Examples 1 to 9 contain oligodextrans of which the degree of polymerization varies with the reaction conditions. It is possible to enrich the product in oligodextrans containing an α(1→2) bond of D.P. 4 and 5 by the action of hydrolases which act exclusively on the α(1→6) and α(1→4) bonds.

The glucoamylase from A. niger hydrolyzes the α(1→4) and α(1→6) bonds in oligodextrans starting from the non-reducing end. Its action is blocked by the presence of an α(1→2) glucoside bond whatever its position on the oligodextran. The endodextranase hydrolyzes only α(1→6) glucoside bonds in an endolytic manner on a substrate with a degree of polymerization greater than or equal to 3. However, endodextranase does not hydrolyze oligodextrans of D.P. 4 and D.P. 5 which contain an α(1→2) glucoside bond at the non-reducing end. The conjugated action of these two enzymes enables a product to be obtained which is made up in teh main of oligodextran of D.P. 4 and oligodextran of D.P. 5.

The fructose liberated in the medium by the action of the glucosyltransferase of L. mesenteroides B-1299 on sucrose and glucose produced by the hydrolases can be separated simultaneously by chromatography on an exchange resin in the calcium form, a known technique widely developed industrially for the production of sirups with a high fructose content.

If a glucoamylase of A. niger is allowed to act on its own, the population of oligodextrans which is obtained has a mean degree of polymerization which is higher than in the preceding case; in fact, the action of the glucoamylase is stopped at the non-reducing end of the oligodextran in the presence of an α(1→2) glucoside bond.

Hydrolysis conditions:
dilution of the synthesis medium to 1/10th
addition of amyloglucosidase NOVO (300 AGU/ml): 3 AGU/ml
addition of dextranase L
AMANO (5000 U/ml): 17 U/ml
temperature: 40° C.
hydrolysis time: 6 hours After incubating for 6 hours, the two enzymes are inactivated by heat (30 minutes, 100° C.). The HPLC analysis of the two reaction media after treatment by the two hydrolases is given in Table 10.

TABLE 10

|  | Oligodextrans containing an α(1 → 2) bond, D.P. 4 | Oligodextrans containing an α(1 → 2) bond, D.P. 5 | Oligodextrans containing an α(1 → 2) bond, D.P. > 5 |
|---|---|---|---|
| Acceptor: maltose Synthesis conditions: see Example 3 | 8 g/l | 17 g/l | 2 g/l |
| Acceptor: isomaltose, isomaltotriose Synthesis conditions: see Example 6 | 22 g/l | 5 g/l | 1 g/l |

EXAMPLE 11

Synthesis and purification of oligodextrans containing an α(1→2) bond with the soluble and insoluble glucosyltransferase from Leuconostoc mesenteroides B-1299

After having prepared and purified the glucosyltransferase as in Example 1(a), the synthesis of the oligodextrans is carried out under the following conditions:
sucrose: 100 g/l
acceptor: Nutriose R 725: 44 g/l (maltose: 33 g/l)
sucrose/maltose ratio: 3
enzyme concentration: 0.3 U/ml
sodium nitride: 0.5%.
pH: 5.6 (adjusted with 1N hydrochloric acid)
temperature: 30° C.
incubation period: 40 hours
reaction volume: 2.5 liters The enzymatic reaction is stopped by heating at 90° C. for 15 minutes.

After synthesis, the composition of the reaction medium is as follows:
fructose: 49 g/l
leucrose: 6 g/l
maltose: 3 g/l
maltotriose: 7.5 g/l
panose: 12 g/l
oligodextran of D.P. 4 containing an α(1→2) bond: 3 g/l
oligodextran of D.P. 4: 13 g/l
oligodextran of D.P. 5 containing an α(1→2) bond: 15 g/l
oligodextrans of D.P.>5 containing an α(1→2) bond: 10 g/l The medium also contains oligodextrans of higher D.P. which do not appear in the chromatographic analysis of the synthesis medium.

The synthesis medium is then subjected to the action of a mixture of glucoamylase from A. niger (3U/ml) and endodextranase from Penicillium sp. (17 U/ml) for 6 hours at 40° C. The enzymatic reaction is stopped by heating at 90° C. for 30 minutes. Glucose and fructose are removed by chromatography on an exchange resin in the calcium form.

40 g of oligodextrans containing an α(1→2) bond of 94% purity are thus obtained. The distribution of the oligodextrans is as follows:

|  | % |
|---|---|
| glucose, leucrose | 6 |
| oligodextrans of D.P. 4 containing an α(1 → 2) bond | 24 |

-continued

| | % |
|---|---|
| oligodextrans of D.P. 5 containing an α(1 → 2) bond | 56 |
| oligodextrans of D.P. 6 containing an α(1 → 2) bond | 7 |
| oligodextrans of D.P. 7 containing an α(1 → 2) bond | 7 |

The preparation is finally lyophilized. After lyophilization the final product is in the form of a white, non-hygroscopic powder without a sugar taste and highly soluble in water. Its solubility in water at 20° C. is 70% (m/m).

EXAMPLE 12

Synthesis of α(1→2) oligodextrans in the presence of oligodextrans of molar mass 1,000 as acceptor The acceptor used is made up of a mixture of linear oligosaccharides containing an α(1→4) bond at the reducing end and α(1→6) bonds exclusively. It is obtained by the action of dextran-saccharase from L. mesenteroides B-512 (F) in the presence of sucrose and maltose.

Experimental conditions

Synthesis 1 sucrose: 200 g/l
oligodextrans of molar mass 1,000 ($M\overline{W}$: 1,000): 20 g/l
20 mM sodium acetate buffer, pH 5.0
temperature: 23° C.
enzyme concentration: 1 U/ml Synthesis 2

Synthesis 1 is repeated except that the concentration of the acceptor (oligodextrans of molar mass 1,000) is 40 g/l.

After 40 hours reaction, the enzyme is inactivated by heat treatment of the reaction medium (heating at 70° C., 20 minutes). The two reaction media are then centrifuged and then subjected to the action of the glucoamylase from Aspergillus niger in order to hydrolyze the α(1→6) glucoside bonds located at the non-reducing end, under the following conditions:

glucoamylase from A. niger AMG 200 L ® (NOVO): 2 AGU/ml
temperature: 40° C.
incubation period: 24 hours The glucoamylase is then inactivated by heating at 70° C. for 20 minutes.

The α(1→2) oligodextrans are then purified by chromatography on an ion exchange resin (Dowex ® 50W×4, in the calcium form) in order to remove the mono- and di-saccharides. The α(1→2) oligodextrans are then subjected to ultrafiltration (cut-off threshold 100,000, AMICON module), demineralized and lyophilized.

In the case of synthesis 1, the mean molar mass by weight ($M\overline{w}$) of the α(1→2) oligodextrans is 1,600. In the case of synthesis 2, the mean molar mass is 1,400.

We claim:

1. A process for the preparation of a mixture comprising oligodextrans a substantial portion of which is comprised of oligodextrans of the general formula (O-α-D-glucopyranosyl-α(1→2))$_m$ (O-α-D-glucopyranosyl-α(1→6))$_n$A, where A is the residue of a sugar acceptor of glucose selected from the group consisting of maltose, isomaltose, isomaltotriose, methyl α-glucoside, and glucose, m is 1 and n is 1, 2 or 3, the position of the α(1→2) glucoside bond being at the non-reducing end or constituting a branching point of each oligodextran, wherein sucrose and a sugar acceptor of glucose selected from the group consisting of maltose, isomaltose, isomaltotriose, methyl α-glucoside, and glucose are brought into contact in the presence of glucosyltransferase enzyme extracted from the strain B-1299 of Leuconostoc mesenteroides for approximately 2 to 48 hours in an aqueous medium.

2. The process of claim 1, wherein the pH is maintained between 4.5 and 6 inclusive during the enzymatic reaction.

3. The process of claim 1, wherein the enzymatic reaction is carried out at a temperature of about 5° to 45° C.

4. The process of claim 1, wherein the weight ratio of sucrose/sugar acceptor of glucose is between 0.5 and 10.

5. The process of claim 4, wherein said ratio of sucrose/sugar acceptor of glucose is between 2 and 4 inclusive.

6. The process of claim 1, wherein the enzyme concentration is between 0.2 and 1.0 units/ml of reaction medium.

7. The process as claimed in claim 13, which includes the supplementary step consisting of subjecting the reaction medium, after removal or inactivation of the glucosyltransferase enzyme, to the action of at least one hydrolase enzyme capable of hydrolyzing α-D-(1→6) glycosidic linkages in order to selectively hydrolyse the oligodextrans which do not contain α(1→2) glucoside bonds present in the reaction medium.

8. The process of claim 7, wherein the hydrolase is the glucoamylase from Aspergillus Niger and/or the endodextranase from Penicillium sp.

9. The process of claim 1 wherein said glucosyltransferase enzyme is present in a soluble or insoluble form.

* * * * *